(12) United States Patent
Tsujii et al.

(10) Patent No.: US 12,036,106 B2
(45) Date of Patent: Jul. 16, 2024

(54) LOW-WEIGHT INFANT DIAPER

(71) Applicant: UNICHARM Corporation, Ehime (JP)

(72) Inventors: Maki Tsujii, Kagawa (JP); Yasuhiro Yamanaka, Kagawa (JP); Satoru Sakaguchi, Kagawa (JP)

(73) Assignee: Unicharm Corporation, Ehime (JP)

( * ) Notice: Subject to any disclaimer, the term of this patent is extended or adjusted under 35 U.S.C. 154(b) by 995 days.

(21) Appl. No.: 17/003,702

(22) Filed: Aug. 26, 2020

(65) Prior Publication Data

US 2020/0390621 A1     Dec. 17, 2020

Related U.S. Application Data

(63) Continuation of application No. PCT/JP2019/006115, filed on Feb. 19, 2019.

(30) Foreign Application Priority Data

Feb. 26, 2018   (JP) ................................. 2018-032265

(51) Int. Cl.
    *A61F 13/64*          (2006.01)
    *A61F 13/49*          (2006.01)
    *A61F 13/58*          (2006.01)

(52) U.S. Cl.
    CPC .... *A61F 13/64* (2013.01); *A61F 2013/49098* (2013.01); *A61F 2013/586* (2013.01)

(58) Field of Classification Search
    CPC ............ A61F 13/64; A61F 2013/49098; A61F 2013/586
    See application file for complete search history.

(56) References Cited

U.S. PATENT DOCUMENTS 3,501,813 A * 3/1970 Lee .......................... D04H 1/72
                                                    19/301
5,386,595 A    2/1995 Kuen et al.
(Continued)

FOREIGN PATENT DOCUMENTS

| CN | 1164994 A | 11/1997 |
|---|---|---|
| CN | 1471901 A | 2/2004 |

(Continued)

OTHER PUBLICATIONS

Office Action issued in corresponding Taiwanese Patent Application No. 107140516 dated Oct. 28, 2021 (5 pages).

(Continued)

*Primary Examiner* — Guy K Townsend
(74) *Attorney, Agent, or Firm* — Osha Bergman Watanabe & Burton LLP

(57) ABSTRACT

A low-weight infant diaper has a longitudinal direction and a width direction that intersect each other. The low-weight infant diaper includes: an exterior sheet disposed closer to a non-skin side than an absorbent body; and a belt including a first locking member on a first side in the width direction and a second locking member on a second side opposite to the first side in the width direction. The belt is locked to a non-skin side of the exterior sheet by the first locking member. The belt includes a first additional joining portion that causes a part of the belt to join the exterior sheet. The first additional joining portion is disposed in a region in the first side.

9 Claims, 10 Drawing Sheets

(56) References Cited

U.S. PATENT DOCUMENTS

| | | | | |
|---|---|---|---|---|
| 5,998,695 | A * | 12/1999 | Roe | A61L 15/18 604/367 |
| 6,018,093 | A * | 1/2000 | Roe | A61L 15/18 604/367 |
| 6,372,952 | B1 * | 4/2002 | Lash | A61F 13/53752 604/378 |
| 6,395,955 | B1 * | 5/2002 | Roe | A61L 15/48 604/362 |
| 6,450,998 | B1 * | 9/2002 | Otsubo | A61F 13/495 604/383 |
| 6,458,111 | B1 * | 10/2002 | Onishi | A61F 13/495 604/385.01 |
| 6,551,295 | B1 * | 4/2003 | Schmidt | A61F 13/5376 604/385.01 |
| 6,570,057 | B1 * | 5/2003 | Schmidt | A61F 13/534 604/378 |
| 6,590,138 | B2 * | 7/2003 | Onishi | A61F 13/532 604/383 |
| 6,626,880 | B2 * | 9/2003 | Onishi | A61K 8/4966 604/383 |
| 6,664,439 | B1 * | 12/2003 | Arndt | A61F 13/15203 604/374 |
| 6,720,471 | B1 * | 4/2004 | Arndt | A61F 13/53747 604/378 |
| 6,869,423 | B2 * | 3/2005 | Onishi | A61F 13/495 604/385.01 |
| 6,897,350 | B2 * | 5/2005 | Yagou | A61F 13/512 604/378 |
| 7,378,567 | B2 * | 5/2008 | Mangold | A61F 13/539 156/196 |
| 7,727,212 | B2 * | 6/2010 | Sakai | A61F 13/539 604/383 |
| 7,772,455 | B1 * | 8/2010 | Roe | A61F 13/51113 604/385.01 |
| 7,838,723 | B1 * | 11/2010 | Schmidt | A61F 13/15203 604/385.01 |
| 8,556,875 | B2 * | 10/2013 | Takahashi | A61F 13/535 604/385.101 |
| 8,927,803 | B2 * | 1/2015 | Sakai | A61F 13/4756 604/385.101 |
| 9,629,758 | B2 * | 4/2017 | Sakaguchi | A61F 13/5323 |
| 10,123,917 | B2 * | 11/2018 | Sakaguchi | A61F 13/625 |
| 10,470,946 | B2 * | 11/2019 | Miyama | A61F 13/5122 |
| 10,675,188 | B2 * | 6/2020 | Ludwig | A61F 13/49017 |
| 11,344,454 | B2 * | 5/2022 | Ludwig | A61F 13/15203 |
| 11,399,992 | B2 * | 8/2022 | Tally | A61F 13/64 |
| 11,452,646 | B2 * | 9/2022 | Tally | A61F 13/4758 |
| 2001/0023339 | A1 * | 9/2001 | Onishi | A61F 13/534 604/383 |
| 2001/0037103 | A1 * | 11/2001 | Onishi | A61F 13/51121 604/385.19 |
| 2001/0053902 | A1 * | 12/2001 | Roe | A61F 13/15 604/385.01 |
| 2002/0026168 | A1 * | 2/2002 | Yagou | A61F 13/512 604/385.01 |
| 2002/0035354 | A1 * | 3/2002 | Mirle | A61F 13/5146 604/385.01 |
| 2002/0091368 | A1 * | 7/2002 | LaVon | A61F 13/15203 604/385.19 |
| 2002/0111594 | A1 * | 8/2002 | Onishi | A61F 13/495 604/385.28 |
| 2003/0045851 | A1 * | 3/2003 | Vartiainen | A61F 13/535 604/383 |
| 2006/0184151 | A1 * | 8/2006 | Onishi | A61F 13/15203 604/385.24 |
| 2006/0287636 | A1 * | 12/2006 | Sakai | A61F 13/532 604/385.101 |
| 2008/0103287 | A1 * | 5/2008 | Chino | C08C 19/22 528/421 |
| 2009/0198207 | A1 | 8/2009 | Torigoshi et al. | |
| 2011/0208147 | A1 * | 8/2011 | Kawakami | A61F 13/5323 604/385.01 |
| 2012/0078209 | A1 * | 3/2012 | Sakai | A61F 13/53 604/378 |
| 2012/0323195 | A1 * | 12/2012 | Ehrnsperger | A61F 13/15 604/366 |
| 2013/0079740 | A1 * | 3/2013 | Ehrnsperger | A61L 15/58 604/367 |
| 2013/0096526 | A1 * | 4/2013 | Schroder | A61F 13/53708 604/374 |
| 2013/0237944 | A1 | 9/2013 | Yamanaka et al. | |
| 2013/0331806 | A1 * | 12/2013 | Rosati | A61F 13/53743 604/366 |
| 2014/0005622 | A1 * | 1/2014 | Wirtz | A61F 13/539 604/366 |
| 2014/0005623 | A1 * | 1/2014 | Wirtz | A61F 13/53418 604/366 |
| 2014/0121487 | A1 * | 5/2014 | Faybishenko | G16H 40/63 600/365 |
| 2015/0057633 | A1 * | 2/2015 | Sakaguchi | A61F 13/49017 604/385.16 |
| 2015/0065981 | A1 * | 3/2015 | Roe | A61F 13/4756 604/378 |
| 2015/0100036 | A1 * | 4/2015 | Sakaguchi | A61F 13/5633 604/385.03 |
| 2015/0157251 | A1 * | 6/2015 | Nelson | A61B 5/6808 600/580 |
| 2015/0282998 | A1 * | 10/2015 | Arizti | A61F 13/51104 604/385.19 |
| 2017/0246043 | A1 | 8/2017 | Ludwig et al. | |
| 2017/0246052 | A1 * | 8/2017 | Ludwig | A61F 13/15585 |
| 2017/0246056 | A1 * | 8/2017 | Tagomori | A61F 13/47272 |
| 2017/0252015 | A1 * | 9/2017 | Barnhorst | A61F 13/42 |
| 2018/0049929 | A1 * | 2/2018 | Konawa | A61F 13/534 |
| 2018/0369029 | A1 * | 12/2018 | Barnhorst | A61F 13/51456 |
| 2019/0240085 | A1 * | 8/2019 | Miyama | A61F 13/5122 |
| 2020/0337914 | A1 * | 10/2020 | Onishi | A61F 13/539 |
| 2020/0390619 | A1 * | 12/2020 | Tsujii | A61F 13/494 |
| 2020/0390620 | A1 * | 12/2020 | Tsujii | A61F 13/56 |
| 2020/0390621 | A1 * | 12/2020 | Tsujii | A61F 13/5633 |

FOREIGN PATENT DOCUMENTS

| | | | | |
|---|---|---|---|---|
| CN | 204133713 U | | 2/2015 | |
| JP | H06218009 A | | 8/1994 | |
| JP | H06218009 A | * | 8/1994 | A61F 13/49 |
| JP | 3059442 A | * | 7/1999 | A61F 13/56 |
| JP | 3059442 U | | 7/1999 | |
| JP | 2005304605 A | | 11/2005 | |
| JP | 2005304605 A | * | 11/2005 | A61F 13/493 |
| JP | 2008253680 A | | 10/2008 | |
| JP | 2008253680 A | * | 10/2008 | A61F 13/493 |
| JP | 2009261823 A | | 11/2009 | |
| JP | 2010068954 A | * | 4/2010 | A61F 13/493 |
| JP | 6585751 B2 | | 10/2019 | |
| TW | 200942216 A | | 10/2009 | |
| TW | 201330837 A | | 8/2013 | |
| TW | 201626969 A | | 8/2016 | |
| WO | 2014/103464 A1 | | 7/2014 | |

OTHER PUBLICATIONS

Office Action issued in the counterpart Japanese Patent Application No. 2019-161024, dated May 25, 2021 (10 pages).

Office Action issued in the corresponding Chinese Patent Application No. 201980015191.X, dated Aug. 13, 2021 (13 pages).

English translation of the International Preliminary Report on Patentability issued in corresponding International Application No. PCT/JP2019/006115, dated Aug. 27, 2020 (7 pages).

International Search Report issued in corresponding International Application No. PCT/JP2019/006115, dated May 7, 2019, with translation (4 pages).

Written Opinion issued in corresponding International Application No. PCT/JP2019/006115, dated May 7, 2019 (5 pages).

(56) References Cited

OTHER PUBLICATIONS

Extended European Search Report issued in corresponding European Patent Application No. 19756711.8 dated Mar. 29, 2021 (6 pages).

* cited by examiner

LOW-WEIGHT INFANT DIAPER

BACKGROUND

Technical Field

The present invention relates to a low-weight infant diaper.

Related Art

Conventional open-type disposable diapers are widely known. With an open-type disposable diaper, two end portions of belt members (e.g., fastening tape or straps) provided on the left and right sides of the diaper main body (e.g., an absorbent main body) are locked to the front side and the back side of the diaper main body in order to put on the diaper. Patent Document 1 discloses a disposable absorbent clothing article (diaper) that has straps (belt members) provided with fasteners (locking members) that can be detachably attached to both the back side and the front side.

PATENT LITERATURE

Patent Document 1: Japanese Patent Application Publication No. H6-218009

According to the disposable diaper in Patent Document 1, the belt members can be attached and detached on the front side and the back side, thus facilitating the operations of putting on and taking off the diaper. For example, when a parent puts such a diaper on an infant, regardless of whether the infant is sleeping in a prone posture or a supine posture, the diaper can be easily put on or taken off on either the front side or the back side.

However, when the diaper is put on, if a portion of a locking member provided on a belt member peels away from the diaper main body, the detached portion of the locking member may become caught on and engaged with the infant's clothing or mat that they are sleeping on, for example, and the belt member may then completely separate from the diaper main body. Particularly in the case where the diaper is intended for a low-weight infant, movement of the low-weight infant's body needs to be minimized in order to reduce the burden placed thereon when the diaper is put on, and therefore if the belt member easily separates from the diaper main body, it becomes difficult to put on the diaper.

SUMMARY

One or more embodiments of the present invention provide a diaper for a low-weight infant that suppresses the separation of a belt member from a main body portion when being put on.

One or more embodiments of the present invention provide a low-weight infant diaper having a longitudinal direction and a width direction that intersect each other,
the low-weight infant diaper including:
an exterior sheet arranged on a non-skin side with respect to an absorbent body; and
a belt member (i.e. belt) that includes a locking member on a one side in the width direction and that includes a locking member on another side in the width direction,
the belt member being locked to a non-skin side of the exterior sheet by the one-side locking member,
an additional joining portion being provided in a one-side region of the belt member,
the additional joining portion being a portion that detachably joins a portion of the belt member to the exterior sheet.

Embodiments of the present invention will be described herein with reference to the drawings. Those skilled in the art will recognize that many alternative embodiments can be accomplished using the teaching of the present invention and that the present invention is not limited to the embodiments illustrated herein for explanatory purposes.

According to one or more embodiments of the present invention, it is possible to provide a diaper for a low-weight infant that suppresses the separation of a belt member from a main body portion when being put on.

DETAILED DESCRIPTION

Figure 1:
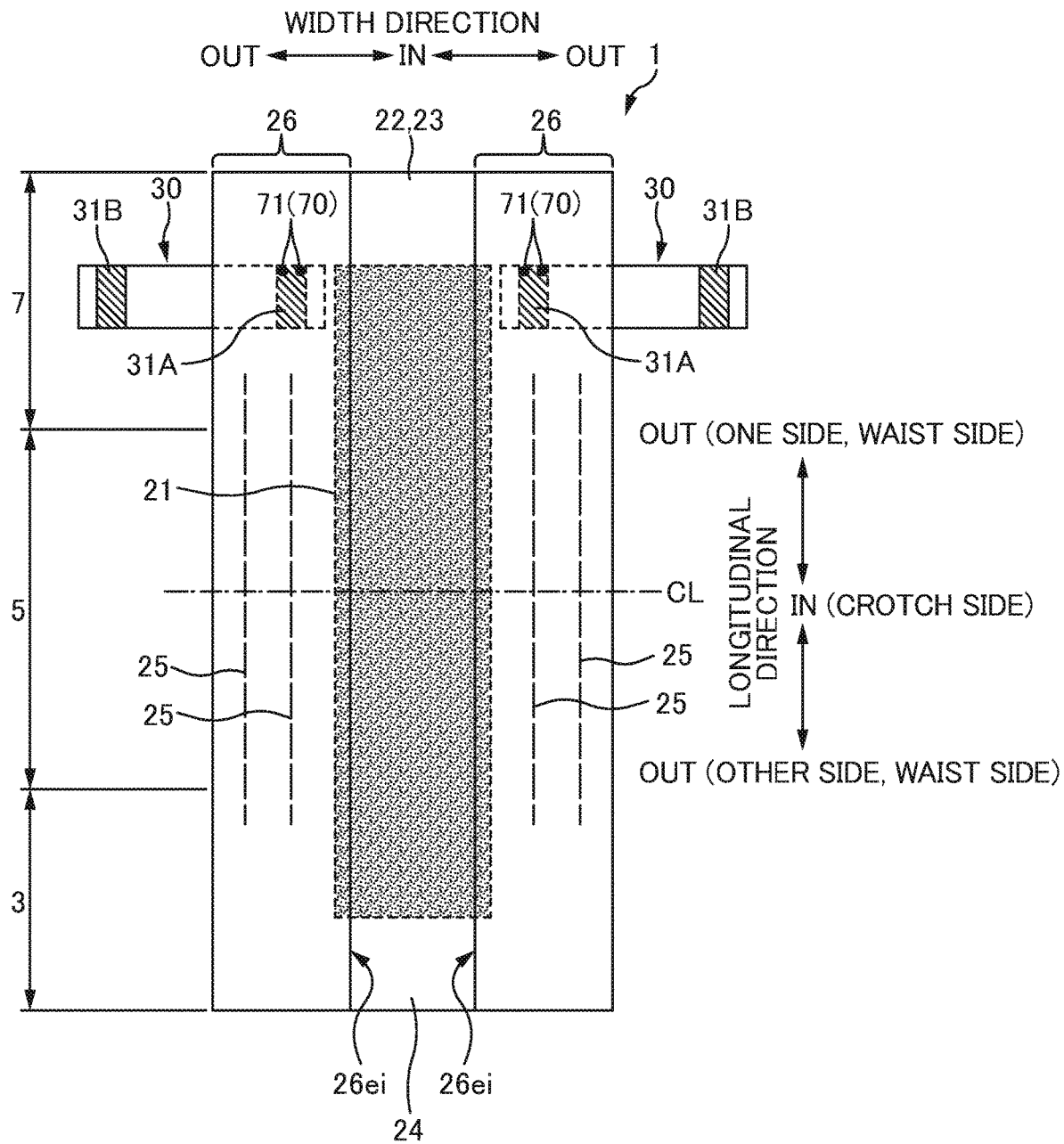
FIG. 1 is a plan view of a diaper 1 in an unfolded and stretched state.

At least the following matters will become clear with the description of this specification and the attached drawings.

A low-weight infant diaper having a longitudinal direction and a width direction that intersect each other,
the low-weight infant diaper including:
an exterior sheet arranged on a non-skin side with respect to an absorbent body; and
a belt member that includes a locking member on a one side in the width direction and that includes a locking member on another side in the width direction,
the belt member being locked to a non-skin side of the exterior sheet by the one-side locking member,
an additional joining portion being provided in a one-side region of the belt member,
the additional joining portion being a portion that detachably joins a portion of the belt member to the exterior sheet.

According to this low-weight infant diaper, the locking of the belt member to the exterior sheet is strengthened by the additional joining portion, and therefore when the diaper is put on a low-weight infant, the locking member is less likely to be peeled away from the exterior sheet, and the separation of the belt member from the main body portion (exterior sheet) of the diaper is easily suppressed.

In one or more embodiments,
the additional joining portion is provided outward in the longitudinal direction with respect to a center of the belt member.

According to this low-weight infant diaper, when the diaper is inserted between a mat or the like and the body of a low-weight infant sleeping thereon, the region of the leading end portion in insertion is less likely to be peeled away, and curling of the belt member is suppressed. This thus makes it possible to further suppress the separation of the belt member.

In one or more embodiments,
the additional joining portion is provided at a location overlapped with the one-side locking member.

According to this low-weight infant diaper, the locking of the locking member (belt member) to the exterior sheet becomes even stronger, thus making it possible to further suppress the separation of the belt member from the main body portion of the diaper.

In one or more embodiments,
a pair of the additional joining portions are respectively provided in two widthwise end portions of the one-side locking member.

According to this low-weight infant diaper, the locking of the corner portion of the locking member to the exterior sheet becomes even stronger. Accordingly, when the diaper is put on a low-weight infant, it is possible to suppress the case where the corner portion of the locking member becomes an origin of peeling, and it is possible to suppress the separation of the belt member.

In one or more embodiments,
the additional joining portions are provided at locations that are overlapped with a longitudinal outward end of the one-side locking member and two widthwise ends of the one-side locking member.

According to this low-weight infant diaper, a gap is less likely to be formed between the locking member and the exterior sheet at the corner of the locking member, and therefore the corner is less likely to become an origin of peeling of the locking member. This makes it possible to further suppress the separation of the belt member from the main body portion of the diaper.

In one or more embodiments,
the additional joining portion is provided at a location not overlapped with the one-side locking member.

According to this low-weight infant diaper, the case where hooks at the surface of the locking member are damaged or crushed by welding is suppressed. Accordingly, even if the belt member is peeled away from the exterior sheet of the diaper and then locked once again to the exterior sheet, the locking strength is less likely to decrease.

In one or more embodiments,
one of the additional joining portions is provided inward in the width direction with respect to an inward end of the one-side locking member, and
another one of the additional joining portions is provided outward in the width direction with respect to an outward end of the one-side locking member.

According to this low-weight infant diaper, the belt member and the exterior sheet are joined in the vicinity of the two widthwise side ends of the locking member, and therefore the locking member is less likely to become peeled away from the exterior sheet when the diaper is put on a low-weight infant. This therefore makes it possible to further suppress the separation of the belt member from the main body portion of the diaper.

In such a low-weight infant diaper, concerning a center position of the additional joining portion that is inward of the inward end of the one-side locking member, a distance between an inward end of the belt member and the center position may be larger in the width direction than a distance between the inward end of the one-side locking member and the center position.

According to this low-weight infant diaper, a joining portion (additional joining portion) is provided for joining the belt member and the exterior sheet at a location closer in the width direction to the inward end of the locking member. Accordingly, when the diaper is put on a low-weight infant, the inward end portion of the locking member is less likely to become peeled away from the exterior sheet. This therefore makes it possible to further suppress the separation of the belt member from the main body portion of the diaper.

In such a low-weight infant diaper, concerning a center position of the additional joining portion that is outward of the outward end of the one-side locking member, a distance between an outward end of the exterior sheet and the center position may be larger in the width direction than a distance between the outward end of the one-side locking member and the center position.

According to this low-weight infant diaper, a joining portion (additional joining portion) is provided for joining the belt member and the exterior sheet at a location closer in the width direction to the outward end of the locking member. Accordingly, when the diaper is put on a low-weight infant, the outward end portion of the locking member is less likely to become peeled away from the exterior sheet. This therefore makes it possible to further suppress the separation of the belt member from the main body portion of the diaper.

In such a low-weight infant diaper, a sum length occupied by the additional joining portion in the belt member in the longitudinal direction may be smaller than a sum length occupied by the additional joining portion in the belt member in the width direction.

According to this low-weight infant diaper, the longitudinal region of the belt member joined by the additional joining portion is smaller, thus allowing the additional joining portion to be easily peeled away when the belt member is pulled along the width direction. On the other hand, the widthwise region of the belt member occupied by the additional joining portion is larger, thus suppressing the peeling away of the additional joining portion when the belt member is pulled along the longitudinal direction. Accordingly, the belt member is less likely to separate from the main body portion of the diaper even if subjected to force along the longitudinal direction when the diaper is put on, whereas the belt member is easily separated from the main body portion of the diaper when subjected to force along the width direction when the diaper is taken off.

In one or more embodiments,
for each additional joining portion,
a longitudinal length of the additional joining portion is shorter than a widthwise length of the additional joining portion.

According to this low-weight infant diaper, the additional joining portions are each easily peeled away when the belt member is pulled in the width direction, but are less likely to be peeled away when the belt member is pulled in the longitudinal direction. Accordingly, the belt member is even less likely to separate from the main body portion of the diaper even if subjected to force along the longitudinal direction when the diaper is put on, whereas the belt member is even more easily separated from the main body portion of the diaper when subjected to force along the width direction when the diaper is taken off.

Basic Configuration of Disposable Diaper 1

A disposable diaper 1 (hereinafter also simply called the diaper 1) according to one or more embodiments is a low-weight infant disposable diaper that is mainly intended for a newborn infant or an infant, and is favorably for use by a low-weight infant, whose body weight is 3000 g or less, and particularly favorably for use by a low-birth-weight infant, whose body weight is less than 2500 g. Note that the concept of a low-weight infant includes not only a low-birth-weight infant (having a body weight less than 2500 g), but also a very-low-birth-weight infant (having a body weight less than 1500 g) and an extremely-low-birth-weight infant (having a body weight less than 1000 g).

Figure 2A:
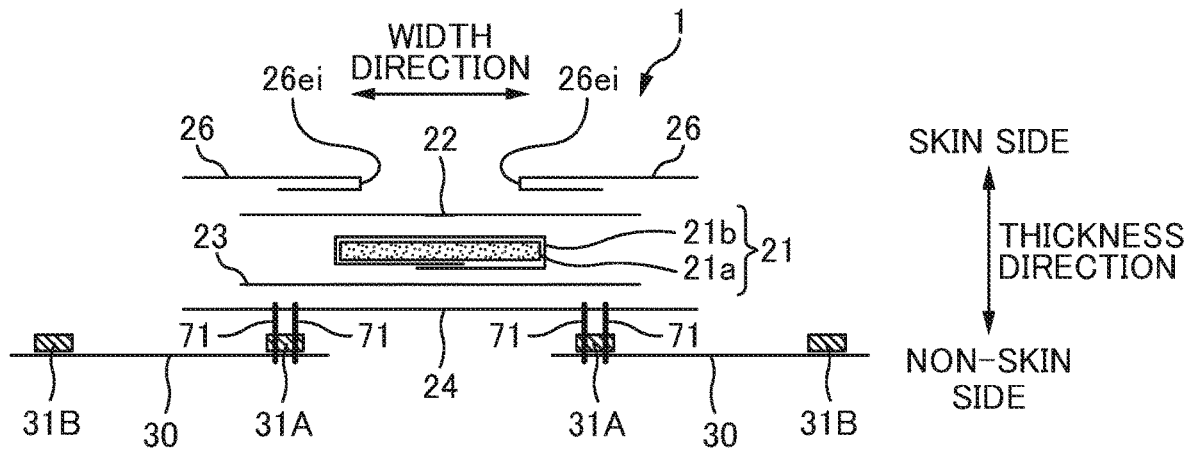
FIG. 2A is an exploded illustrative view of a schematic cross-section of a back portion 7 of the diaper 1.
Figure 2B:
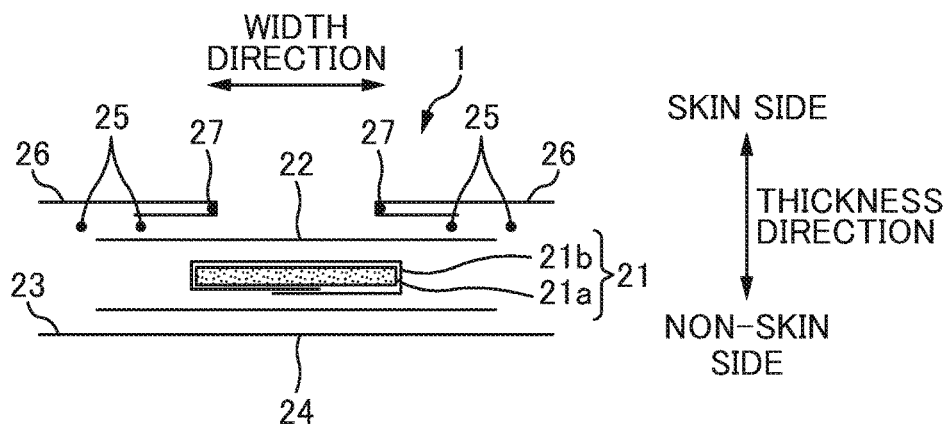
FIG. 2B is an exploded illustrative view of a schematic cross-section of a crotch portion 5 of the diaper 1.

FIG. 1 is a plan view of the diaper 1 in an unfolded and stretched state. FIG. 2A is an exploded illustrative view of a schematic cross-section of a back portion 7 of the diaper 1. FIG. 2B is an exploded illustrative view of a schematic cross-section of a crotch portion 5 of the diaper 1. Note that the unfolded and stretched state of the diaper 1 refers to a state in which the diaper 1 has been unfolded and stretched such that wrinkles in the diaper 1 are substantially no longer visible, that is to say a state in which the diaper 1 has been stretched such that the lengths of constituent members of the diaper 1 (e.g., a later-described top sheet 22 and the like) match or are close to the dimensions of the members on their own.

The diaper 1 according to one or more embodiments is a so-called open-type disposable diaper, and as shown in FIG. 1, includes a front portion 3, a crotch portion 5, and a back portion 7. The front portion 3 is the portion that is located on the front portion side (front side, front waist side) of the wearer. Also, the back portion 7 is the portion that is located on the back portion side (back side, back waist side) of the wearer. Note that the front portion 3 and the back portion 7 are defined in this way for the sake of convenience, but the front portion 3 and the back portion 7 can be switched when the diaper 1 is used (worn). In other words, the back portion 7 may be located on the front side of the wearer, and the front portion 3 may be located on the back side of the wearer. The crotch portion 5 is the portion that is located between the front portion 3 and the back portion 7.

As shown in FIG. 1, the directions used in the following descriptions are defined as follows. The direction from the front portion 3 toward the back portion 7 is the "longitudinal direction", and the "width direction" is a direction orthogonal to the longitudinal direction. The line CL in FIG. 1 denotes a line that indicates the center of the diaper 1 in the longitudinal direction. Also, as shown in FIG. 2, the "thickness direction" is a direction orthogonal to the longitudinal direction and the width direction, and in this direction, the side corresponding to the wearer's skin is the "skin side", and the side opposite thereto is the "non-skin side".

The diaper 1 includes a main body portion 10 and belt members 30.

Main Body Portion 10

The main body portion 10 is the portion that absorbs and holds a fluid such as urine excreted by the wearer, and as shown in FIG. 1, is constituted by the front portion 3, the crotch portion 5, and the back portion 7, and is substantially rectangular in a plan view. The main body portion 10 mainly includes an absorbent body 21, a top sheet 22, a leak-proof sheet 23, a back sheet 24, and side sheets 26 (see FIGS. 2A and 2B).

The absorbent body 21 includes an absorbent core 21a constituted by layers of a liquid absorbent material that can absorb excrement such as urine, and is arranged extended over the front portion 3, the crotch portion 5, and the back portion 7. The dotted region in FIG. 1 indicates the region occupied by the absorbent core 21a. The absorbent body 21 (absorbent core 21a) according to one or more embodiments is substantially rectangular and elongated in the longitudinal direction. Note that the shape of the absorbent body 21 is not intended to be limited to the shape shown in FIG. 1, and need only be provided in at least the crotch portion 5. Also, the absorbent body 21 may be configured such that the absorbent core 21a is covered by a core-wrapping sheet 21b.

The absorbent body 21 according to one or more embodiments is arranged so as to be sandwiched between the top sheet 22 and the leak-proof sheet 23 in the thickness direction. The liquid absorbent material that constitutes the absorbent body 21 can be made of liquid absorbent fibers such as pulp fibers, or liquid-absorbent particulate matter such as a superabsorbent polymer. The liquid absorbent material may include a liquid absorbent material other than liquid absorbent fibers and liquid-absorbent particulate matter.

The top sheet 22 is a liquid-permeable member arranged on the skin side of the absorbent body 21, and is made of nonwoven fabric, for example. The leak-proof sheet 23 is a liquid-impermeable member arranged on the non-skin side of the absorbent body 21, and is constituted by a resin film sheet, for example. The back sheet 24 is a member (exterior sheet) that constitutes the exterior of the non-skin side of the diaper 1, and is made of nonwoven fabric, for example. The back sheet 24 is arranged on the non-skin side of the leak-proof sheet 23 (see FIGS. 2A and 2B).

At least the crotch portion 5 of the main body portion 10 is provided with leg elastic members 25 (e.g., elastic strings; see FIG. 2B) that can stretch and contract in the longitudinal direction and are arranged between the side sheets 26 and the back sheet 24 (the top sheet 22 in FIG. 2B). The leg elastic members 25 are members that give the main body portion 10 stretchability in the crotch portion 5. In one or more embodiments, the leg elastic members 25 are attached in a state of being stretched in the longitudinal direction. The leg elastic members 25 thus give the main body portion 10 contractive force in the longitudinal direction. When the diaper 1 is put on, the crotch portion 5 contracts along the longitudinal direction, and thus the main body portion 10 three-dimensionally deforms into a rounded shape that curves along the wearer's body, the two widthwise side portions of the main body portion 10 contract, and leg gathers are formed around the wearer's legs. Accordingly, the main body portion 10 is held in a shape that wraps around the wearer's crotch, thus improving the fit of the diaper 1. This also facilitates suppressing the case where excrement leaks from around the wearer's legs to the outside of the diaper 1.

The side sheets 26 are a pair of members provided on the skin side in the thickness direction with respect to the top sheet 22 and on the two widthwise sides, and are made of nonwoven fabric, for example. In widthwise outward end regions, the side sheets 26 are joined to the top sheet 22 and the back sheet 24 in the thickness direction. Also, as shown in FIGS. 2A and 2B, the side sheets 26 are folded outward at widthwise inward ends 26ei such that the folded portions are overlaid thereon in the thickness direction. Between the portions of the folded side sheets 26 in the thickness direction, provided are LSG elastic members 27 (e.g., elastic strings) that can stretch and contract in the longitudinal direction. The LSG elastic members 27 are members that give the side sheets 26 stretchability in the crotch portion 5. In one or more embodiments, the LSG elastic members 27 are attached in a state of being stretched in the longitudinal direction, and the LSG elastic members 27 exhibit contractive force in the longitudinal direction. When the diaper 1 is put on, the LSG elastic members 27 contract in the longitudinal direction, and thus the portions of the side sheets 26 that are not joined to the top sheet 22 (back sheet 24) rise up toward the wearer's skin, and the side sheets 26 function as leak-proof walls that suppress the lateral leakage of excrement or the like.

Belt Members 30

The belt members 30 are respectively arranged at the two widthwise side portions of the main body portion 10 in the back portion 7 (back side) of the diaper 1 (see FIG. 1). The belt members 30 according to one or more embodiments each include a locking member 31 on both widthwise one side (inward side) or the widthwise other side (outward side), and the locking members 31 can be locked to the exterior sheet (back sheet 24) of the diaper 1. The locking members 31 are members having hooks that project in the thickness direction, and are constituted by hook-and-loop fasteners or the like. The hooks (not shown) of the locking members 31 become caught on the fibers at the surface of the nonwoven fabric that constitutes the exterior sheet (back sheet 24) of the diaper 1, and thus the belt members 30 are locked to the main body portion 10 (exterior sheet) via the locking member 31.

As shown in FIGS. 1 and 2, the belt members 30 according to one or more embodiments each include the locking member 31 on both the widthwise one side (inward side) and the widthwise other side (outward side). Accordingly, both widthwise sides of the belt members 30 can be locked to exterior sheet (back sheet 24) of the diaper 1. Hereinafter, the locking member 31 provided on the widthwise inward side will also be called an inward locking member 31A, and the locking member 31 provided on the widthwise outward side will also be called an outward locking member 31B. In FIG. 2, the belt members 30 are locked to the non-skin side of the back sheet 24 (exterior sheet) by the inward locking members 31A arranged on the widthwise inward side. Also, the belt members 30 and the back sheet 24 (exterior sheet) are joined by additional joining portions 70. The additional joining portions 70 will be described in detail later.

Figure 3A:
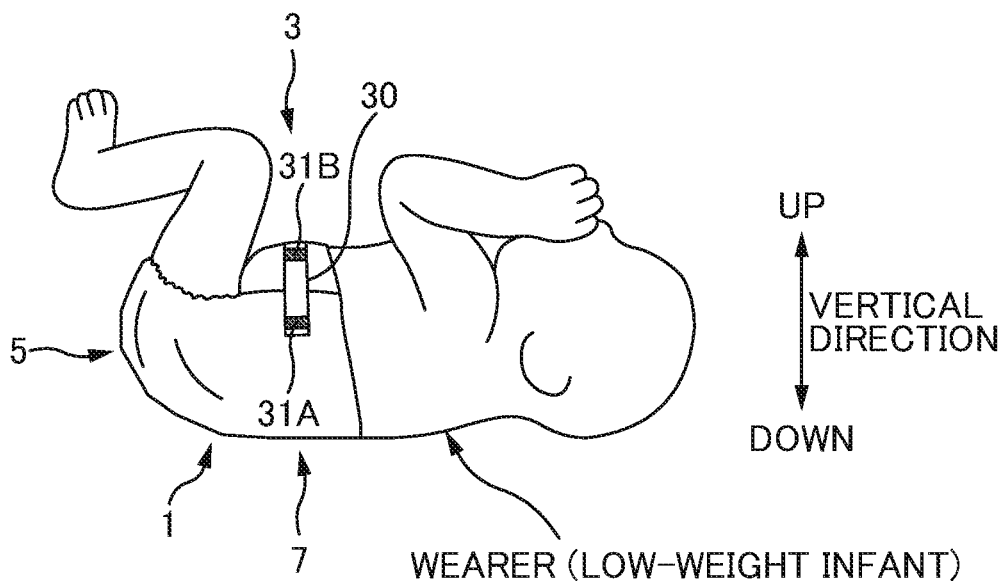
FIGS. 3A and 3B are diagrams showing the diaper 1 in a put-on state.
Figure 3B:
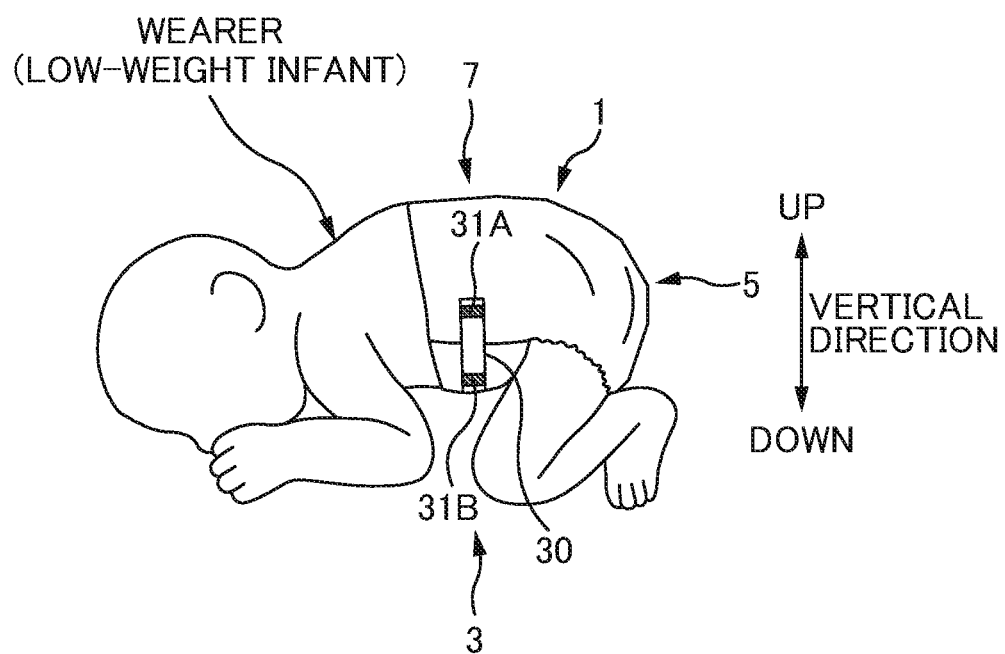

When the diaper 1 is put on, the outward locking members 31B arranged on the widthwise outward side are locked to the non-skin side of the back sheet 24 (exterior sheet) in the front portion 3 (front side) of the main body portion 10, thus forming a waist opening and a pair of leg openings of the diaper 1, and therefore the position of the diaper 1 can be fixed on the wearer's body (waist) (see FIGS. 3A and 3B). Note that the front portion 3 of the diaper 1 may be provided with target tape (not shown), which is for facilitating the locking of the outward locking members 31B, in a region that is on the non-skin side in the thickness direction in the widthwise central portion of the back sheet 24. Also, a configuration is possible in which, when the diaper 1 is put on, the waist opening is formed by the outward locking member 31B of the widthwise one-side belt member 30 being locked to the non-skin-side surface of the widthwise other-side belt member 30.

The longitudinal product length of the diaper 1 for a low-weight infant according to one or more embodiments (the dimension in the state where the product is stretched in the longitudinal direction so as to eliminate wrinkles) is in the range of 170 to 330 mm. For example, the product length of the diaper 1 is 310 mm in the case of being for a low-birth-weight infant having a body weight less than 2500 g, the product length of the diaper 1 is 270 mm in the case of being for a very-low-birth-weight infant having a body weight less than 1500 g, and the product length of the diaper 1 is 170 mm in the case of being for an extremely-low-birth-weight infant having a body weight less than 1000 g.

Also, the waist dimension of the diaper 1 for a low-weight infant according to one or more embodiments is in the range of 160 to 295 mm. Note that the waist dimension is the dimension in the state where the widthwise outward end portion of one of the belt members 30 is aligned with the widthwise inward end portion of the other belt member 30, and the product is stretched to eliminate wrinkles. In other words, it is a dimension in the state where the product is stretched in the width direction. For example, the waist dimension of the diaper 1 is 273.5 mm in the case of being for a low-birth-weight infant, and the waist dimension of the diaper 1 is 220 mm in the case of being for a very-low-birth-weight infant having a body weight less than 1500 g.

Operation of Putting on Diaper 1

The following describes operations when putting the diaper 1 on a low-weight infant who is the intended wearer. FIGS. 3A and 3B are diagrams showing the diaper 1 in a put-on state.

When an open-type disposable diaper such as the diaper 1 is put on, first, the back portion 7 of the diaper 1 in the unfolded state is arranged at the back part of the intended wearer, the crotch portion 5 is placed against the wearer's crotch part, and the front portion 3 is placed against the wearer's stomach part. Then the pair of belt members 30, which are locked to the two widthwise sides of the main body portion 10 in the back portion 7 (back side), are wrapped around the wearer's waist from the back side toward the front side, and the outward locking members 31B are locked to the non-skin side of the front portion 3 (front side) so as to fix the diaper 1 around the wearer's waist. The diaper 1 is can thus be put on the intended wearer as shown FIG. 3A. Conversely, when the diaper 1 is taken off, the operations are performed in the reverse of when being put on, that is to say, the outward locking members 31B, which are locked to the back sheet 24 (exterior sheet) in the front portion 3 (front side), are peeled off to release the waist portion, and the diaper 1 can thus being taken off easily.

Note that low-weight infants, which are the intended wearer of the diaper 1 according to one or more embodiments, are generally placed in an incubator to grow in a hospital or the like. For this reason, when the diaper for a low-weight infant is put on or taken off, the worker (person who is putting the diaper on the low-weight infant or taking it off) needs to put their hand through an operation window provided in the incubator and perform the task in a small space. Also, it is common for the low-weight infant to be placed in the incubator in a prone posture in which their back is curved in a C shape and their legs are sharply bent into an M shape, as shown in FIG. 3B. This posture will also be called the "positioning posture", which is a posture that is close to the posture taken in the mother's womb (fetus-like bent posture) and is a calming posture. When the low-weight infant is in the positioning posture, the outward locking members 31B are located below the stomach of the wearer (low-weight infant) as shown in FIG. 3B.

Accordingly, conventionally, when performing the task of changing the diaper on a low-weight infant that is in the positioning posture in an incubator, the worker has needed to put their hand under the low-weight infant's stomach inside the small space and peel off the outward locking members 31B of the belt members 30. In contrast, with the diaper 1 according to one or more embodiments, the inward locking members 31A of the belt members 30 can be peeled off the back sheet 24 (exterior sheet). For this reason, as shown in FIG. 3B, the worker can easily peel off the inward locking members 31A on the back side of the low-weight infant. Accordingly, the diaper can be changed without subjecting the low-weight infant to the burden of a change in posture, for example. Furthermore, the diaper 1 according to one or more embodiments can be put on backwards such that the front portion 3 is on the back side and the back portion 7 is on the front side, and therefore regardless of the posture of the low-weight infant when sleeping, the diaper 1 can be easily put on or taken off without moving the low-weight infant's body, thus making the diaper 1 favorable for low-weight infants.

Figure 4A:
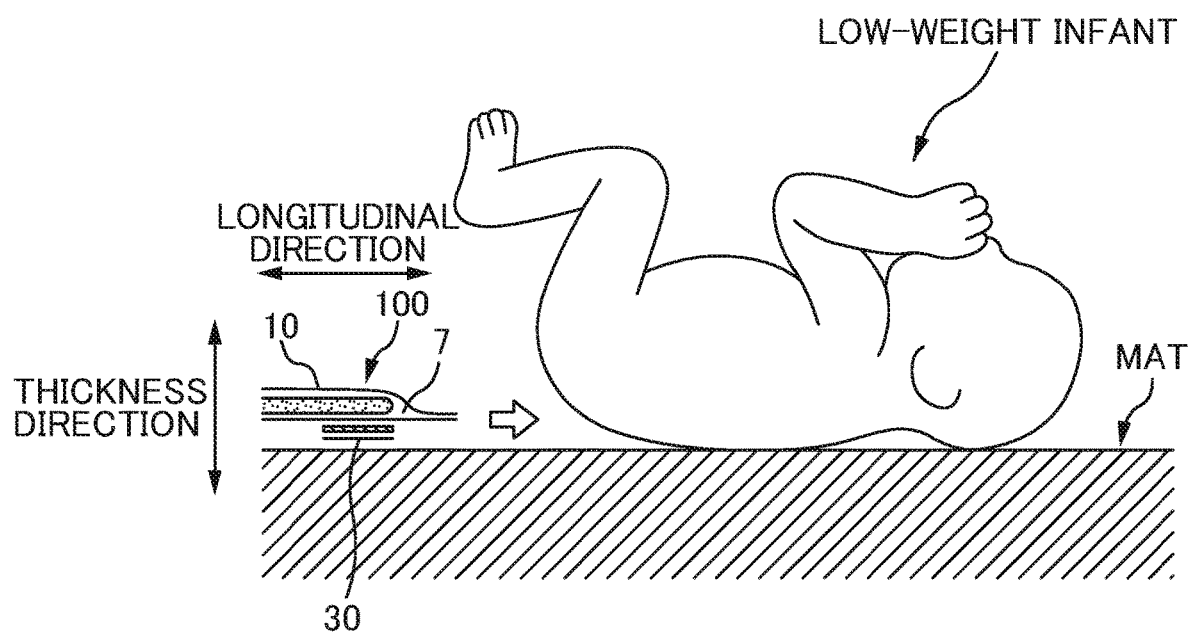
FIGS. 4A and 4B are diagrams illustrating an operation of putting a diaper 100 according to a comparative example on a low-weight infant.
Figure 4B:
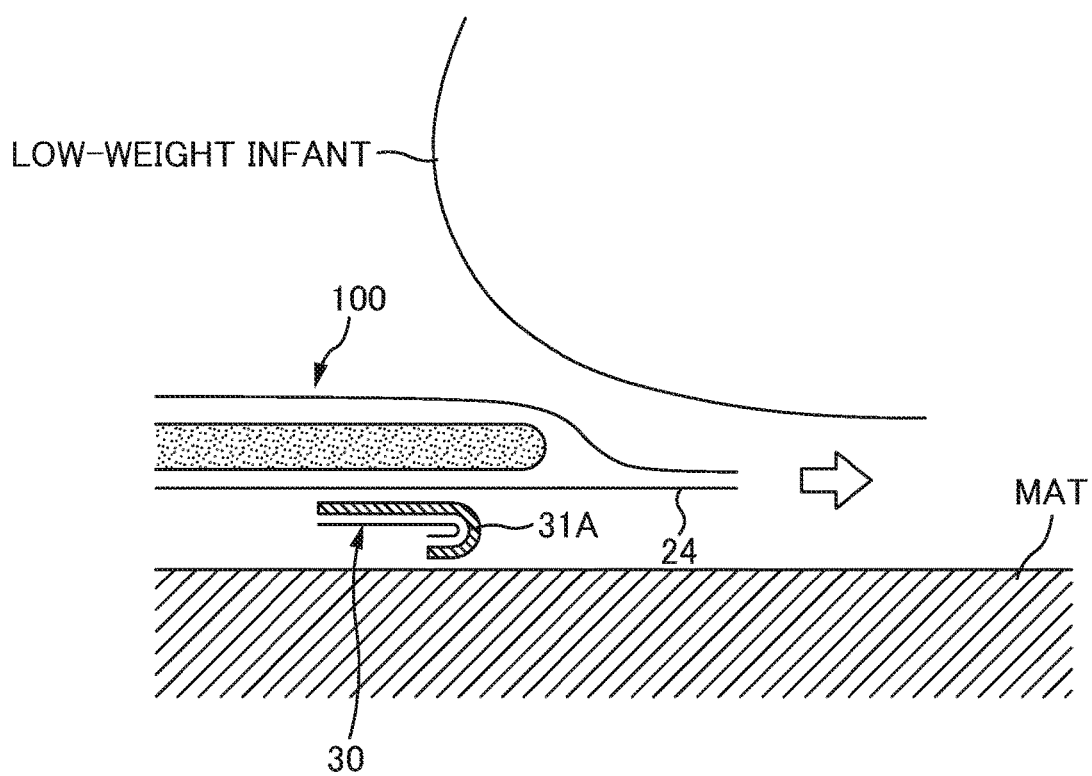

Also, in the case of a diaper having a structure in which the belt members are locked to the main body portion with use of locking members on the two widthwise sides, as with the diaper 1, sometimes the belt members become detached from the main body portion due to the locking members locked to the main body portion becoming unintendedly peeled off when the diaper is put on. FIGS. 4A and 4B are diagrams illustrating an operation of putting a diaper 100 according to a comparative example on a low-weight infant. The diaper 100 of the comparative example does not include the additional joining portions 70 for joining the belt members 30 to the main body portion 10. Specifically, the belt members 30 are simply locked to the exterior sheet (back sheet 24) with use of the inward locking members 31A, which are hook-and-loop fasteners or the like, and the belt members 30 (inward locking members 31A) can be easily peeled away the exterior sheet. The configuration of the diaper 100 of the comparative example is similar to that of the diaper 1 according to one or more embodiments with the exception of the additional joining portions 70.

FIG. 4A is a side view of the case where the diaper 100 is put on a low-weight infant who is sleeping face-up on a mat. First, the back portion 7 of the diaper 100 is arranged at the back part of the low-weight infant. Specifically, the back portion 7 of the unfolded diaper 100 is arranged between the low-weight infant's body and the mat by being inserted under the low-weight infant's crotch. At this time, in order to reduce the burden placed on the low-weight infant's body, rather than lifting up the low-weight infant's body, the diaper 100 is pressed downward toward the mat (i.e., vertically downward) while the back portion 7 of the diaper 100 is inserted between the low-weight infant's back part and the mat.

Due to the diaper 100 being pressed against the mat, frictional force is likely to act between the belt members 30 and the mat, and portions of the locking members 31 (inward locking members 31A) sometimes become peeled away from the back sheet 24 (exterior sheet) due to outward ends of the belt member 30 becoming curled up in the longitudinal direction as shown in FIG. 4B. There is a risk as follow: the inward locking members 31A that peeled away from the exterior sheet then engage with the mat, and when the diaper 100 is further inserted under the low-weight infant's back part, the inward locking members 31A become entirely peeled away from the back sheet 24, and the belt members 30 become entirely separated from the main body portion 10. If the belt members 30 become separated, the locking members 31 need to be re-locked to the main body portion 10 (back sheet 24), and the operation shown in FIG. 4A needs to be performed again, thus placing a burden on the low-weight infant's body.

Additional Joining Portions 70

Figure 5:
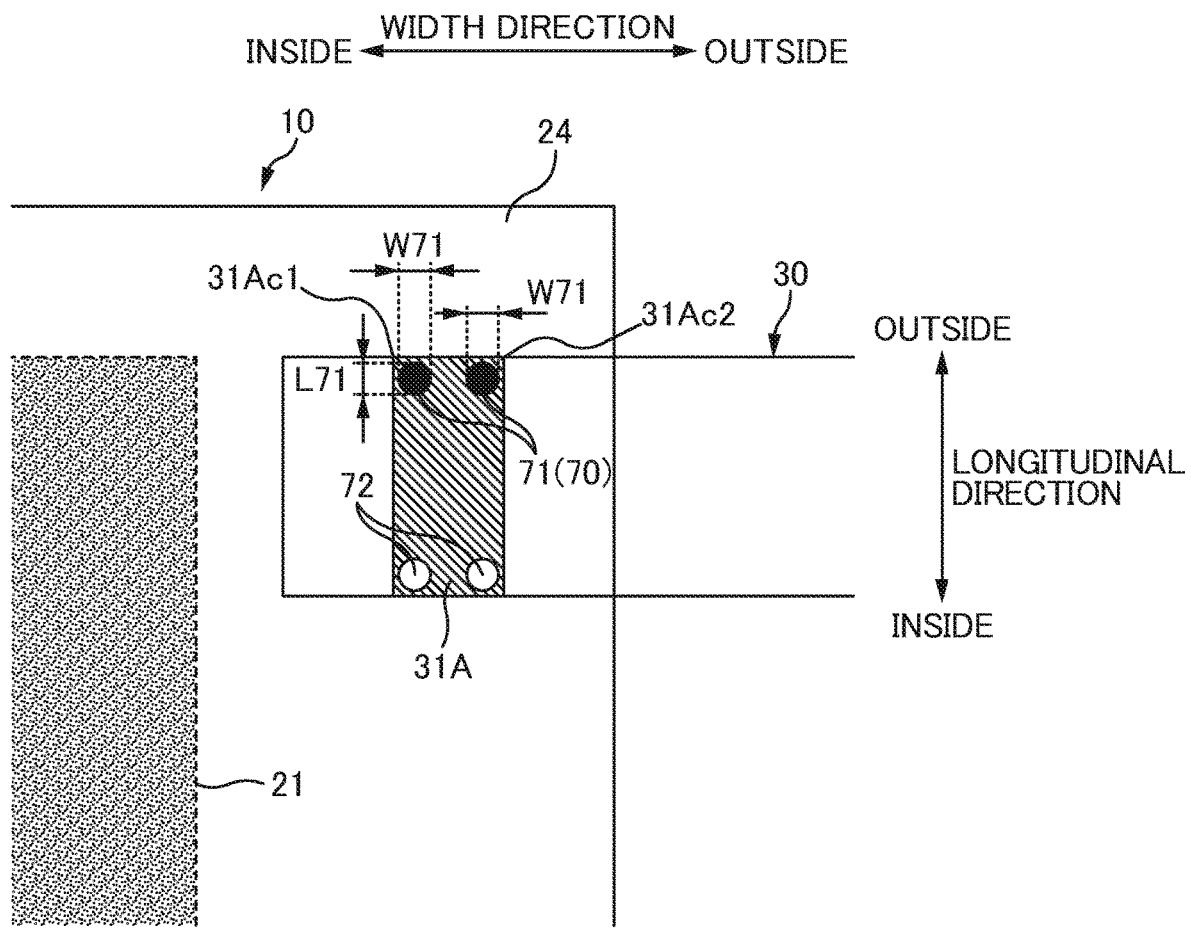
FIG. 5 is an enlarged plan view illustrating the arrangement of additional joining portions 70.

In contrast, in the diaper 1 according to one or more embodiments, the additional joining portions 70 are provided between the belt members 30 and the back sheet 24 (exterior sheet) of the main body portion 10, thus making it possible to suppress separation of the belt members 30 from the main body portion 10 when the diaper 1 is put on. FIG. 5 is an enlarged plan view illustrating the arrangement of the additional joining portions 70.

The additional joining portions 70 are formed by using a known welding means (e.g., heat sealing or sonic sealing) to join portions of the belt members 30 to the back sheet 24 (exterior sheet). In FIG. 5, a pair of additional joining portions 71, which are shown as black circles, are provided at positions that are outward in the longitudinal direction with respect to the center of the belt member 30 and in two widthwise end portions of the inward locking member 31A. In FIG. 5, the pair of additional joining portions 71 are substantially circular (dot-shaped) and have a longitudinal length L71 and a widthwise length W71 that are substantially equivalent to each other. Also, the pair of additional joining portions 71 are arranged at the same position in the longitudinal direction. Note that the shape of the pair of additional joining portions 71 is not limited to this, and they may have different shapes from each other. Also, the positions of the pair of additional joining portions 71 are not required to be the same in the longitudinal direction.

Note that in FIG. 5, two additional joining portions 72, which are shown as white circles, are provided at locations inward in the longitudinal direction with respect to the center of the belt member 30. Providing the additional joining portions 72 in addition to the additional joining portions 71 makes it possible to further suppress separation of the belt member 30 when the diaper 1 is put on, but it is not necessarily required that the additional joining portions 72 be provided.

Figure 6:
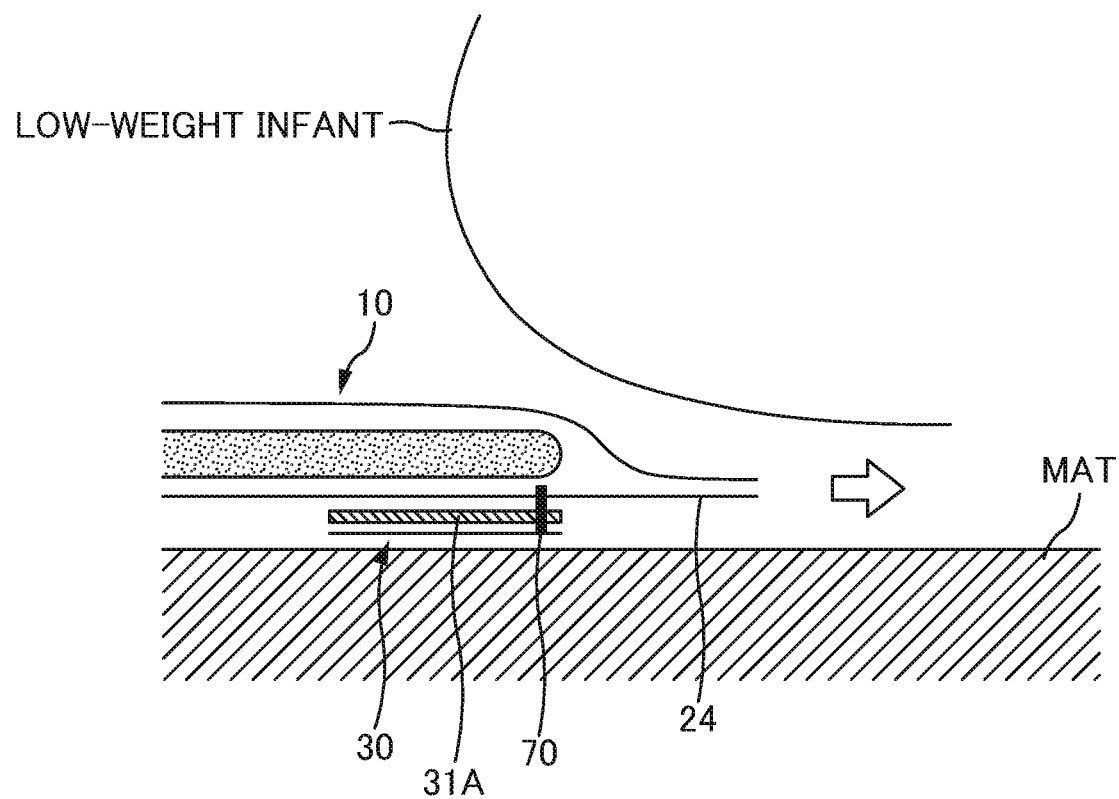
FIG. 6 is a diagram illustrating an operation of putting the diaper 1 on a low-weight infant.

Providing the additional joining portions 70 suppresses the peeling of the belt members 30 away from the exterior sheet (back sheet 24) of the main body portion 10 when the diaper 1 is put on. FIG. 6 is a diagram illustrating the operation of putting the diaper 1 according to one or more embodiments on a low-weight infant, and corresponds to FIG. 4B that illustrates the operation of putting on the diaper 100 of the comparative example.

In the case of putting the diaper 1 on a low-weight infant who is sleeping in a supine posture, similarly to the case described using FIG. 4A, the back portion 7 of the diaper 1 in the unfolded state is arranged between the low-weight infant's body and the mat by being inserted under the low-weight infant's crotch. At this time, due to the belt members 30 and the main body portion 10 being joined by the additional joining portions 71 at longitudinally outward positions of the belt members 30 (i.e., positions in the vicinity of the leading end portions in the operation inserting the diaper 1), suppressed is the curling of the longitudinal outward ends of the belt members 30 shown in FIG. 4B. Accordingly, the inward locking members 31A are less likely to peel away from the exterior sheet (back sheet 24), suppressing the separation of the belt members 30 from the main body portion 10 during the operation of putting on the diaper 1. Note that although the additional joining portions 70 (71) are provided outward in the longitudinal direction with respect to the center of the belt member 30 in FIG. 5, the effect of suppressing the separation of the belt member 30 from the main body portion 10 is obtained even if the additional joining portions 70 (e.g., the additional joining portions 72 in FIG. 5) are provided at the center or inward thereof in the longitudinal direction.

Also, due to the additional joining portions 71 (70) being provided so as to be overlapped with the inward locking member 31A in FIG. 5, the locking of the inward locking member 31A to the exterior sheet (back sheet 24) becomes even stronger, and the separation of the belt member 30 is suppressed even further.

Also, it may be that the positions at which the additional joining portions 70 are provided are as close as possible to the outer peripheral edges of the inward locking members 31A. When the inward locking members 31A peel away from the exterior sheet (back sheet 24), peeling is highly likely to begin at a corner portion of the outer peripheral edges of the inward locking members 31A, particularly in the case where the inward locking members 31A are rectangular. Accordingly, strengthening the locking at such portions makes it possible to further suppress separation of the belt members 30. In one or more embodiments, two additional joining portions 71 are respectively provided at positions that are in two widthwise end portions and in a longitudinal outward end portions of the inward locking members 31A, and therefore the locking of the inward locking members 31A to the exterior sheet (back sheet 24) is strong in the corner portions of the inward locking members 31A, and separation of the belt members 30 is likely to be suppressed.

Furthermore, additional joining portions 70 may be formed at corners 31Ac1 and 31Ac2 that are intersections between the longitudinal outward end of the inward locking member 31A and the two widthwise ends of the inward locking member 31A. In other words, the corners 31Ac1 and 31Ac2 of the inward locking member 31A may be joined to the exterior sheet (back sheet 24). According to this configuration, at the corners 31Ac1 and 31Ac2, the inward locking member 31A and the exterior sheet (back sheet 24) are joined without a gap in the thickness direction, thus suppressing the formation of peeling origin points, and further suppressing the separation of the belt member 30.

Note that in the diaper 1, the belt members 30 can be freely attached to and detached from the front portion 3 and the back portion 7 of the main body portion 10 as described above, thus preventing a burden from being placed on the low-weight infant's body when the diaper 1 is put on and taken off. Accordingly, the additional joining portions 70 that join the inward locking members 31A to the exterior sheet (back sheet 24) need to be able to be easily peeled off by a person's strength. In other words, the additional joining portions 70 need to detachably join the belt members 30 to the exterior sheet (back sheet 24). In one or more embodiments, as shown in FIG. 5, two dot-shaped additional joining portions 71 are provided in one portion of each inward locking member 31A. These additional joining portions 70 (71) are less likely to be peeled away by force commensurate with frictional force generated between the belt member 30 and the mat when the diaper is put on (see FIG. 6). However, when the diaper is taken off, these additional joining portions can be easily peeled away when a person forcefully pulls the belt member 30.

Note that when the belt member 30 is to be detached from the back portion 7 of the main body portion 10, the main body portion 10 is grabbed with one hand, a widthwise end portion of the belt member 30 is grabbed with the other hand, and the grabbed portions are pulled away from each other in the width direction, thus peeling away the locking member 31 (inward locking member 31A). Accordingly, the additional joining portions 70 may be easily peeled away when subjected to force along the width direction. On the other hand, when the diaper 1 is put on as described using FIG. 6, the locking member 31 (inward locking member 31A) is subjected to force along the longitudinal direction, and therefore the additional joining portions 70 may be not likely to be peeled away when subjected to force along the longitudinal direction.

In view of this, in the diaper 1, the additional joining portions 70 are formed such that a sum value $\sigma W70$ of the widthwise length occupied by the additional joining portions 70 in the belt member 30 is larger than a sum value $\sigma L70$ of the longitudinal length occupied by the additional joining portions 70 ($\sigma W70 > \sigma L70$). In the example in FIG. 5, the sum value $\sigma W71$ (=2W71) of the length occupied by the pair of additional joining portions 71 in the width direction is greater than the sum value $\sigma L71$ (=L71) of the length occupied by the pair of additional joining portions 71 in the longitudinal direction ($\sigma W71 > \sigma L71$).

According to this configuration, the longitudinal region of the belt member 30 occupied by the additional joining portions 70 is smaller, thus allowing the additional joining portions 70 to be easily peeled away when the belt member 30 is pulled along the width direction. On the other hand, the widthwise region of the belt member 30 occupied by the additional joining portions 70 is larger, thus suppressing the peeling away of the additional joining portions 70 when the belt member 30 is pulled along the longitudinal direction.

Figure 7A:
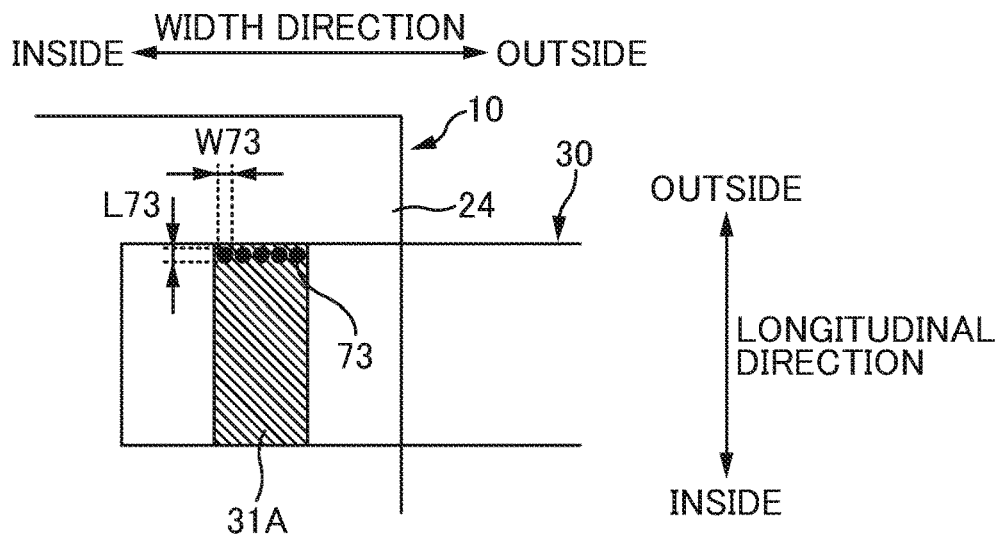
FIGS. 7A to 7C are schematic plan views of variations of the additional joining portions 70.
Figure 7B:
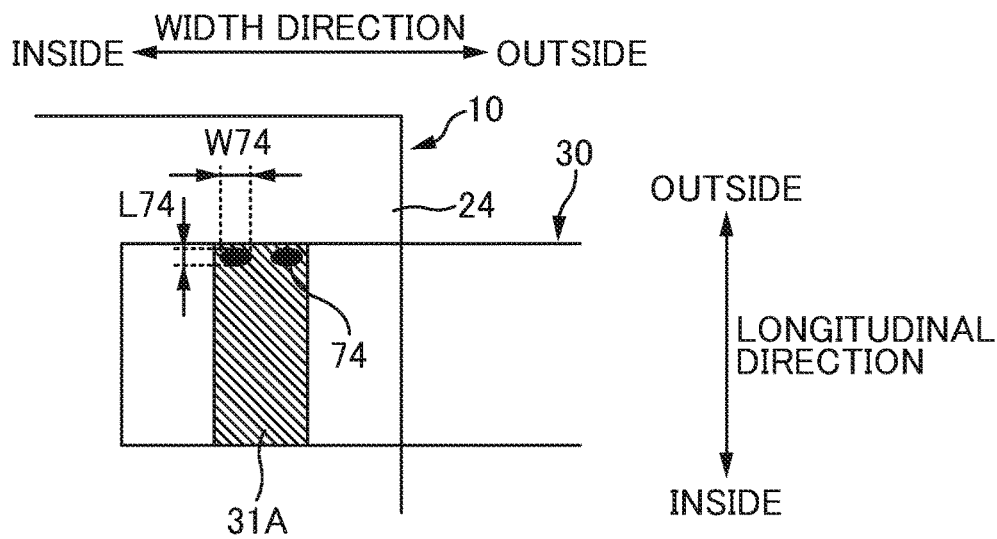
Figure 7C:
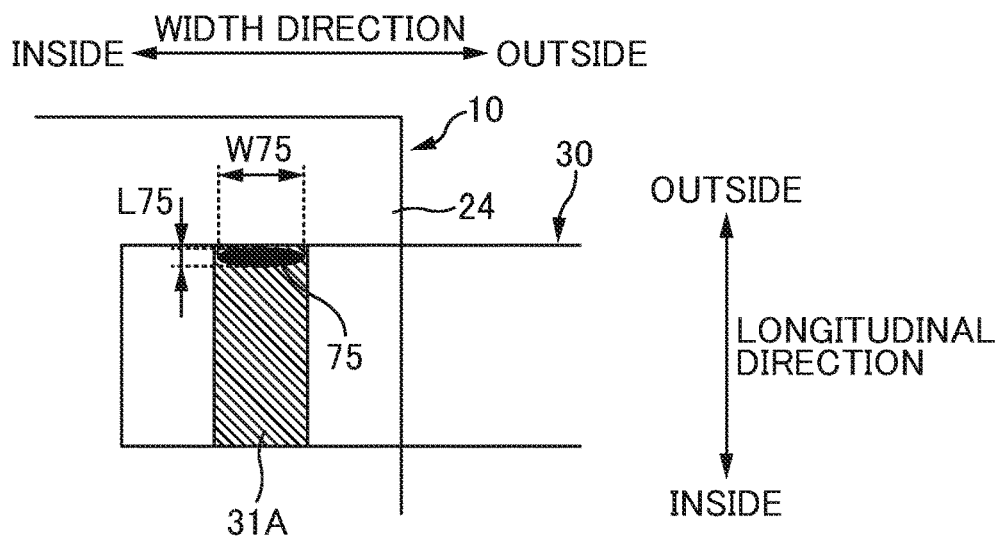

FIGS. 7A to 7C are schematic plan views of variations of the additional joining portions 70.

In FIG. 7A, additional joining portions 73 that have the same shape as the additional joining portions 71 in FIG. 5 are provided side-by-side along the width direction. In the case shown in FIG. 7A as well, a sum value $\sigma W73$ of the widthwise length occupied by the additional joining portions 73 in the belt member 30 is larger than a sum value $\sigma L73$ of the longitudinal length occupied by the additional joining portions 73 ($\sigma W73 > \sigma L73$). Accordingly, the additional joining portions 73 of the belt member 30 are not likely to be peeled away when subjected to force along the longitudinal direction when the diaper 1 is put on. On the other hand, these additional joining portions are easily peeled away when the belt member 30 is subjected to force along the width direction when the diaper 1 is taken off.

In FIG. 7B, in contrast with the additional joining portions 71 in FIG. 5, two additional joining portions 74 are substantially shaped as ellipses that are elongated in the width direction. In the case shown in FIG. 7B as well, a sum value $\sigma W74$ of the widthwise length occupied by the additional joining portions 74 in the belt member 30 is larger than a sum value $\sigma L74$ of the longitudinal length occupied by the additional joining portions 74 ($\sigma W74 > \sigma L74$). Furthermore, with each additional joining portion 74 as well, a length W74 occupied in the width direction is larger than a length L74 occupied in the longitudinal direction (W74>L74), and therefore the additional joining portions 74 of the belt member 30 are even less likely to be peeled away when subjected to force along the longitudinal direction when the diaper 1 is put on.

In FIG. 7C, there is only one additional joining portion 75 that is substantially shaped as an ellipse that is longer in the width direction than the additional joining portions 74 in FIG. 7B. In the case shown in FIG. 7C as well, a sum value $\sigma W75$ of the widthwise length occupied by the additional joining portion 75 in the belt member 30 is larger than a sum value $\sigma L75$ of the longitudinal length occupied by the additional joining portion 75 ($\sigma W75 > \sigma L75$). Furthermore, similarly to FIG. 7B, with the additional joining portion 75 itself, a length W75 occupied in the width direction is larger than a length L75 occupied in the longitudinal direction (W75>L75). Accordingly, the additional joining portion 75 of the belt member 30 is even less likely to be peeled away when subjected to force along the longitudinal direction when the diaper 1 is put on.

Figure 8:
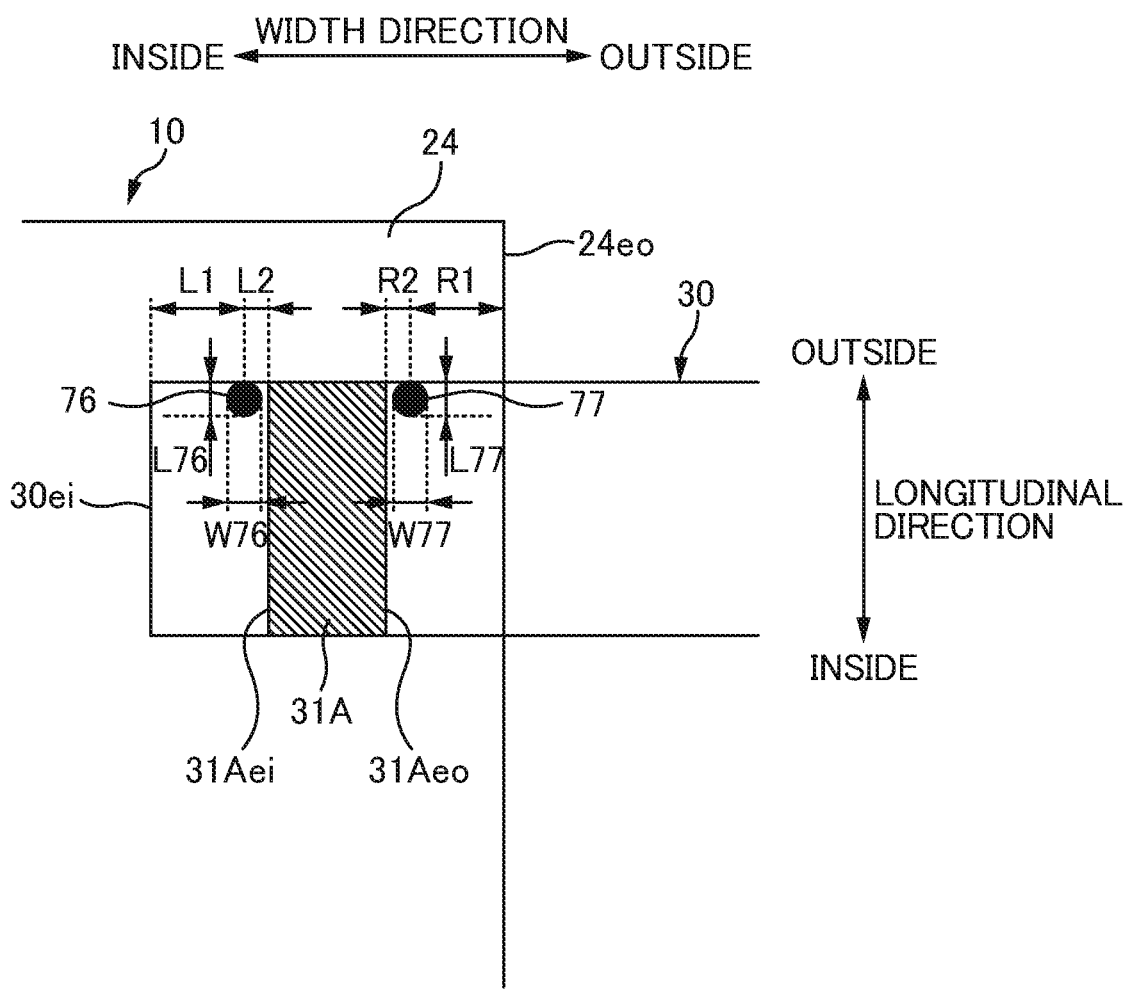
FIG. 8 is a schematic plan view of a case where additional joining portions 70 are provided outside an inward locking member 31A in the width direction.

Also, although the additional joining portions 70 are provided at positions overlapped with the inward locking members 31A in the belt members 30 in the above-described example, the additional joining portions 70 may be provided at positions not overlapped with the inward locking members 31A. FIG. 8 is a schematic plan view of a case where additional joining portions 70 are provided outside the inward locking member 31A in the width direction.

In FIG. 8, an additional joining portion 76, which is shown as a black circle, is provided at a position that is outward in the longitudinal direction with respect to the center of the belt member 30 and inward in the width direction with respect to an inward end 31Aei of the inward locking member 31A. Similarly, an additional joining portion 77, which is shown as a black circle, is provided at a position that is outward in the longitudinal direction with respect to the center of the belt member 30 and outward in the width direction with respect to an outward end 31Aeo of the inward locking member 31A. Note that although the additional joining portion 76 and the additional joining portion 77 shown in FIG. 8 have the same shape, they may have shapes that are different from each other.

As shown in FIG. 8, even if the additional joining portions 70 are provided at positions not overlapped with the inward locking member 31A, it is possible to obtain effects similar to those of the additional joining portions 71 described using FIGS. 5 and 6. In other words, in the case of putting the diaper 1 on a low-weight infant, even when the diaper 1 is inserted between the low-weight infant's body and the mat, the inward locking members 31A are not likely to be peeled away from the exterior sheet (back sheet 24), and it is possible to suppress the separation of the belt members 30 from the main body portion 10. Also, the hooks (not shown) at the surface of the inward locking members 31A are not likely to be damaged or crushed by welding. This therefore suppresses a reduction in locking strength when the inward locking members 31A are peeled away from the exterior sheet (back sheet 24) and then locked once again.

Also, the sum value W76+W77 of the widthwise lengths occupied by the additional joining portion 76 and the additional joining portion 77 in the belt member 30 is larger than the sum value L76(≈L77) of the longitudinal lengths occupied by the additional joining portion 76 and the additional joining portion 77. Accordingly, similarly to the case described above, the additional joining portion 76 and the additional joining portion 77 are not likely to be peeled away when subjected to force along the longitudinal direction when the diaper 1 is put on, but are easily peeled away when subjected to force along the width direction when the diaper 1 is taken off.

Even if the additional joining portions 70 are provided at positions not overlapped with the inward locking member 31A, the additional joining portions 70 may be arranged as close as possible to the outer peripheral edges of the inward locking member 31A. With respect to the width direction in FIG. 8, the additional joining portion 76 that is inside the inward locking member 31A is arranged closer to the inward end of the inward locking member 31A than to the inward end of the belt member 30. In other words, with respect to the width direction, a distance L1 between an inward end 30ei of the belt member 30 and the center position of the additional joining portion 76 is larger than a distance L2 between the center position of the additional joining portion 76 and the inward end 31Aei of the inward locking member 31A (L1>L2). Accordingly, when the diaper 1 is put on, the inward end 31Aei (corner 31Ac1) of the inward locking member 31A is not likely to become peeled away, and the separation of the belt member 30 from the main body portion 10 is suppressed.

Similarly, with respect to the width direction, the additional joining portion 77 that is outside to the inward locking member 31A is arranged closer to the outward end of the inward locking member 31A than to the outward end of the belt member 30. In other words, with respect to the width direction, a distance R1 between an outward end 24eo of the back sheet 24 (exterior sheet) and the center position of the additional joining portion 77 is larger than a distance L2 between the center position of the additional joining portion 77 and the outward end 31Aeo of the inward locking member 31A (R1>R2). Accordingly, when the diaper 1 is put on, the outward end 31Aeo (corner 31Ac2) of the inward locking member 31A is not likely to become peeled away, and the separation of the belt member 30 from the main body portion 10 is suppressed.

Variations of Diaper

Figure 9:
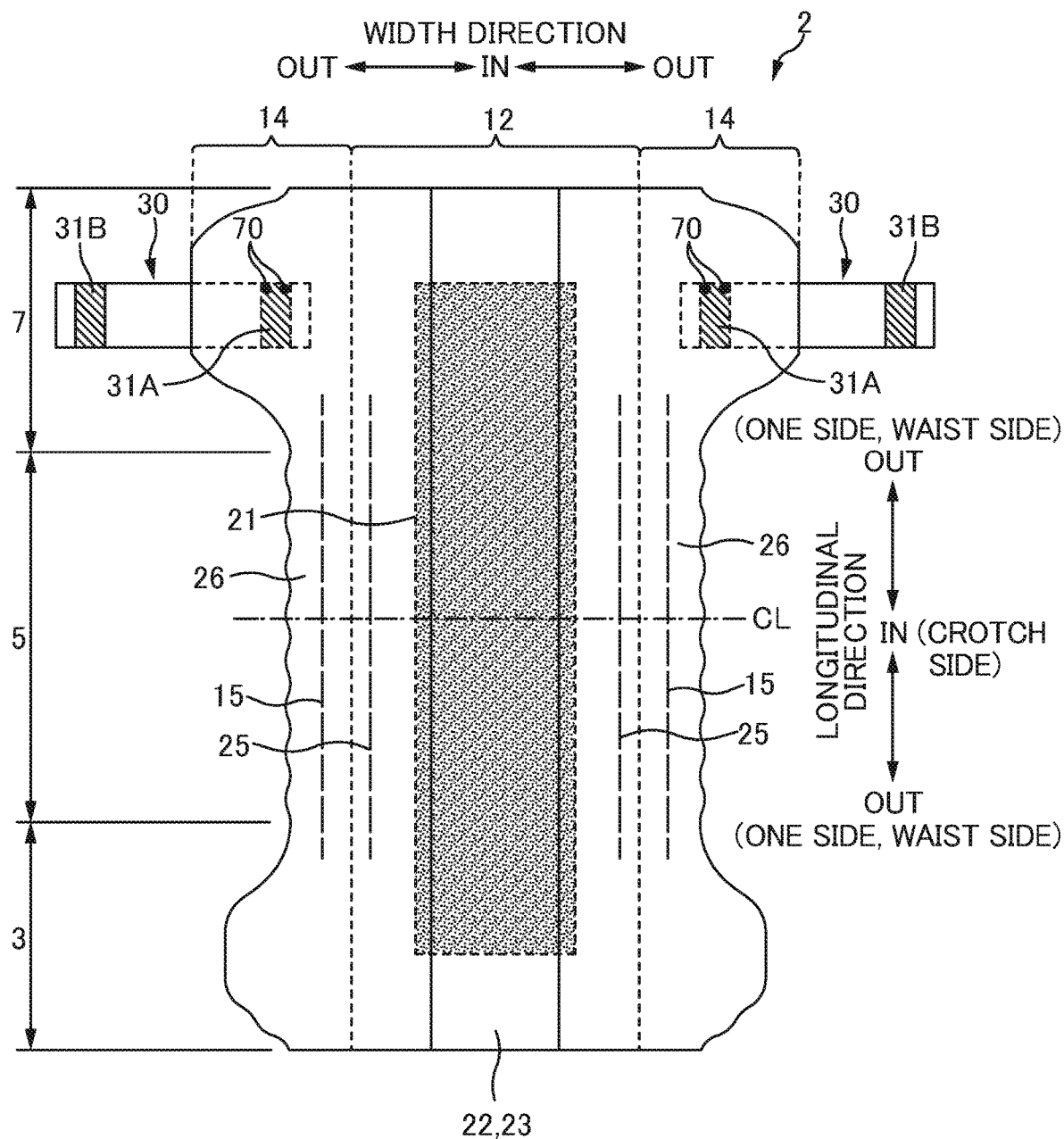
FIG. 9 is a plan view of a diaper 2 in an unfolded and stretched state.
Figure 10:
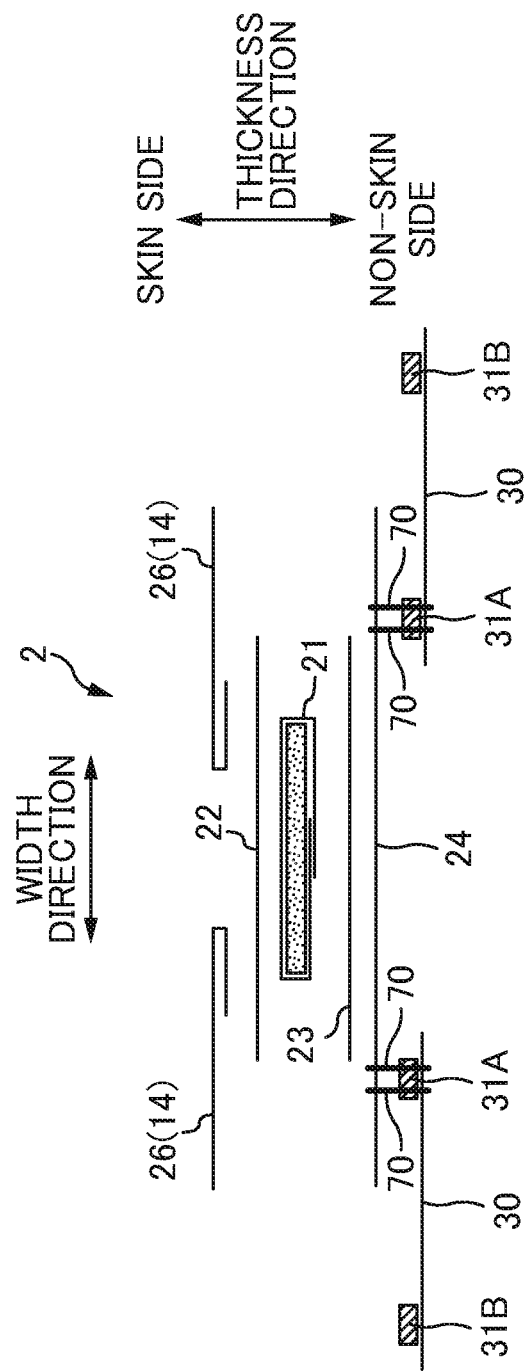
FIG. 10 is an exploded illustrative view of a back portion 7 of the diaper 2.

Although the example where the main body portion 10 of the diaper 1 is substantially rectangular as shown in FIG. 1 is described in the above embodiments, the configuration of the diaper 1 may be changed as follows. FIG. 9 is a plan view of a diaper 2 in an unfolded and stretched state, as a variation of the diaper 1. FIG. 10 is an exploded illustrative view of the back portion 7 of the diaper 2.

The main body portion 10 of the diaper 2 has a central band-shaped region 12 and side flaps 14. The central band-shaped region 12 is a band-shaped region that is constituted by the front portion 3, the crotch portion 5, and the back portion 7, and that is located in the central portion in the width direction. The central band-shaped region 12 is the region that corresponds to the main body portion 10 in the diaper 1. The central band-shaped region 12 mainly includes the absorbent body 21, the top sheet 22, the leak-proof sheet 23, and the back sheet 24 (exterior sheet).

The side flaps 14 are portions located at the two widthwise side portions of the central band-shaped region 12. The side flaps 14 extend over the front portion 3, the crotch portion 5, and the back portion 7. The widthwise length (width) of the side flaps 14 in the crotch portion 5 is smaller than the widthwise length (width) of the side flaps 14 in the front portion 3 and the back portion 7. The side flaps 14 are mainly constituted by the side sheets 26 and the back sheet 24 (see FIG. 10).

The pair of side flaps 14 are each provided with side-flap elastic members 15 that stretch and contract in the longitudinal direction. The side-flap elastic members 15 are elastic members such as elastic strings that stretch and contract in the longitudinal direction, and are members that give the leg openings stretchability when the diaper 2 is put on. In other words, the side-flap elastic members 15 are leg elastic members that allow the leg opening portions of the diaper 2 to fit around the wearer's legs. Also, leg gathers are configured by the side-flap elastic members 15 giving stretchability to the side sheets 26 and the back sheet 24 in the crotch portion 5.

In the diaper 2, the belt members 30 are arranged at the two widthwise side portions of the side flaps 14 in the back portion 7 of the diaper 2 (see FIG. 9). Similar to the configuration in the diaper 1, the belt members 30 each include locking members 31 (31A, 31B) constituted by hook-and-loop fasteners or the like on respective sides in the width direction, and the belt members 30 are locked to the non-skin side of the side flaps 14, that is to say to the back sheet 24 (exterior sheet), by the inward locking members 31A arranged on the widthwise inward side. Portions of the belt members 30 and the side flaps 14 (back sheet 24) are joined by the additional joining portions 70.

The configurations and functions of the additional joining portions 70 are similar to those in the diaper 1. In other words, due to the provision of the additional joining portions 70, when the diaper 2 is put on a low-weight infant, the curling of the outward ends of the belt members 30 in the longitudinal direction as described using FIG. 4B is suppressed. Accordingly, the inward locking members 31A are not likely to peel away from the exterior sheet (back sheet 24), and the separation of the belt members 30 from the side flaps 14 during the operation of putting on the diaper 2 is suppressed.

OTHER EMBODIMENTS

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 disposable diaper (diaper),
2 disposable diaper (diaper),
3 front portion, 5 crotch portion, 7 back portion,
10 main body portion,
12 central band-shaped region,
14 side flap,
15 side-flap elastic member,
21 absorbent body, 21a absorbent core, 21b core-wrapping sheet,
22 top sheet, 23 leak-proof sheet,
24 back sheet (exterior sheet),
25 leg elastic member,
26 side sheet,
27 LSG elastic member,
30 belt member,
31 locking member,
31A inward locking member, 31B outward locking member,
70 additional joining portion,
71-77 additional joining portion,
100 disposable diaper (comparative example)

What is claimed is:

1. A low-weight infant diaper having a longitudinal direction and a width direction that intersect each other, the low-weight infant diaper comprising:
   an exterior sheet disposed closer to a non-skin side than an absorbent body; and
   a belt that comprises:
      a first locking member on a first side in the width direction; and
      a second locking member on a second side opposite to the first side in the width direction, wherein
   the belt is locked to a non-skin side of the exterior sheet by the first locking member,
   the belt comprises a first additional joining portion that causes a part of the belt to join the exterior sheet,
   the first additional joining portion is disposed in a region in the first side and overlaps the first locking member,
   the belt further comprises a second additional joining portion, and
   the first and second additional joining portions are respectively disposed in two widthwise end portions of the first locking member.

2. The low-weight infant diaper according to claim 1, wherein the first additional joining portion is disposed outward in the longitudinal direction farther than a center of the belt.

3. The low-weight infant diaper according to claim 1, wherein
   the first and second additional joining portions are disposed at an outward end of the longitudinal direction in the first locking member, and
   the first and second additional joining portions are disposed at both ends of the width direction in the first locking member, respectively.

4. The low-weight infant diaper according to claim 1, wherein the first additional joining portion is not overlapped with the first locking member in the belt.

5. A low-weight infant diaper having a longitudinal direction and a width direction that intersect each other, the low-weight infant diaper comprising:
   an exterior sheet disposed closer to a non-skin side than an absorbent body; and
   a belt that comprises:
      a first locking member on a first side in the width direction; and
      a second locking member on a second side opposite to the first side in the width direction, wherein
   the belt is locked to a non-skin side of the exterior sheet by the first locking member,
   the belt comprises a first additional joining portion that causes a part of the belt to join the exterior sheet,
   the first additional joining portion is disposed in a region in the first side and is not overlapped with the first locking member in the belt,
   the belt further comprises a second additional joining portion,
   the first additional joining portion is disposed inward in the width direction nearer than an inward end of the first locking member, and
   the second additional joining portion is disposed outward in the width direction farther than an outward end of the first locking member.

6. The low-weight infant diaper according to claim 5, wherein in the width direction, a distance between an inward end of the belt and a center position of the first additional joining portion is longer than a distance between the inward end of the first locking member and the center position.

7. The low-weight infant diaper according to claim 5, wherein in the width direction, a distance between an outward end of the exterior sheet and a center position of the second additional joining portion is longer than a distance between the outward end of the first locking member and the center position.

8. A low-weight infant diaper having a longitudinal direction and a width direction that intersect each other, the low-weight infant diaper comprising:
   an exterior sheet disposed closer to a non-skin side than an absorbent body; and a belt that comprises:
  a first locking member on a first side in the width direction; and
  a second locking member on a second side opposite to the first side in the width direction, wherein
the belt is locked to a non-skin side of the exterior sheet by the first locking member,
the belt comprises a first additional joining portion that causes a part of the belt to join the exterior sheet,
the first additional joining portion is disposed in a region in the first side,
the belt further comprises one or more other additional joining portions, and
a sum length occupied by the first additional joining portion and the one or more other additional joining portions in the belt in the longitudinal direction is shorter than a sum length occupied by the first additional joining portion and the one or more other additional joining portions in the belt in the width direction.

9. The low-weight infant diaper according to claim 8, wherein a longitudinal length of each of the first additional joining portion and the one or more other additional joining portions is shorter than a widthwise length of each of the first additional joining portion and the one or more other additional joining portions.

* * * * *